United States Patent [19]

De Rosa et al.

[11] Patent Number: 5,723,576
[45] Date of Patent: Mar. 3, 1998

[54] THROMBIN INHIBITORS, THE PREPARATION THEREOF AND THE USE THEREOF FOR THERAPEUTICAL, PROPHYLACTIC AND DIAGNOSTIC APPLICATIONS

[75] Inventors: Alfredo De Rosa; Armando Rossi, both of Naples, Italy

[73] Assignee: Development Biotechnological Processes S.N.C., Avellino, Italy

[21] Appl. No.: 532,567

[22] PCT Filed: Apr. 13, 1994

[86] PCT No.: PCT/EP94/01144

§ 371 Date: Oct. 16, 1995

§ 102(e) Date: Oct. 16, 1995

[87] PCT Pub. No.: WO94/24156

PCT Pub. Date: Oct. 27, 1994

[30] Foreign Application Priority Data

Apr. 16, 1993 [IT] Italy ................................ MI93A0748

[51] Int. Cl.$^6$ .......................... C07K 14/00; A61K 38/16
[52] U.S. Cl. ........................ 530/324; 514/12; 424/1.69
[58] Field of Search .................. 530/324; 514/12; 424/1.69

[56] References Cited

U.S. PATENT DOCUMENTS 5,256,559 10/1993 Maraganore et al. ............ 435/240.2

FOREIGN PATENT DOCUMENTS

91/02750 3/1991 WIPO .
91/19734 12/1991 WIPO .

OTHER PUBLICATIONS

Maraganore et al., "Design and Characterization of Hirulogs: A novel class of Bivalent Peptide Inhibitors of Thrombin", Biochemistry, vol. 29, pp. 7095–7101, 1990.

Szewczuk et al, "Desing of a Linker for Trivalent Thrombin Inhibitors: Interaction of the Main Chain of the Linker with Thrombin", Biochemistry, vol. 32, pp. 3396–3404, 1993.

*Primary Examiner*—Cecilia J. Tsang
*Assistant Examiner*—Anish Gupta
*Attorney, Agent, or Firm*—Oblon, Spivak, McClelland, Maier & Neustadt, P.C.

[57] ABSTRACT

Peptides having 25 to 27 amino acids capable of binding both to the catalytic site and to the non-catalytic site of hirudin.

9 Claims, No Drawings

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /product="Ala at position 6 is
            D-Ala"

( i x ) FEATURE:
        ( A ) NAME/KEY: Modified-site
        ( B ) LOCATION: 7
        ( D ) OTHER INFORMATION: /product="Ala at position 7 is
            beta-Ala"

( i x ) FEATURE:
        ( A ) NAME/KEY: Modified-site
        ( B ) LOCATION: 8
        ( D ) OTHER INFORMATION: /product="Ala at position 8 is
            beta-Ala"

( i x ) FEATURE:
        ( A ) NAME/KEY: Modified-site
        ( B ) LOCATION: 22
        ( D ) OTHER INFORMATION: /product="Xaa at position 22 is
            Aib"

( i x ) FEATURE:
        ( A ) NAME/KEY: Modified-site
        ( B ) LOCATION: 23
        ( D ) OTHER INFORMATION: /product="Xaa at position 23 is
            Aib"

( x i ) SEQUENCE DESCRIPTION: SEQ ID NO:1:

```
Ile  Arg  Tyr  Thr  Asp  Ala  Ala  Ala  Pro  Glu  Asn  His  Asn  Asn  Gly  Asp
 1              5                        10                       15

Phe  Glu  Glu  Ile  Pro  Xaa  Xaa  Tyr  Leu  Glu
           20                       25
```

( 2 ) INFORMATION FOR SEQ ID NO:2:

( i ) SEQUENCE CHARACTERISTICS:
        ( A ) LENGTH: 26 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 6
        ( D ) OTHER INFORMATION: /product="Ala at position 6 is
            D-Ala"

( i x ) FEATURE:
        ( A ) NAME/KEY: Modified-site
        ( B ) LOCATION: 8
        ( D ) OTHER INFORMATION: /product="Ala at position 8 is
            beta-Ala"

( i x ) FEATURE:

(A) NAME/KEY: Modified-site
            (B) LOCATION: 13
            (D) OTHER INFORMATION: /product="Phe at position 13 is
                b-Phe"

(ix) FEATURE:
            (A) NAME/KEY: Modified-site
            (B) LOCATION: 22
            (D) OTHER INFORMATION: /product="Xaa at position 22 is
                Aib"

(ix) FEATURE:
            (A) NAME/KEY: Modified-site
            (B) LOCATION: 23
            (D) OTHER INFORMATION: /product="Xaa at position 23 is
                Aib"

(ix) FEATURE:
            (A) NAME/KEY: Modified-site
            (B) LOCATION: 25
            (D) OTHER INFORMATION: /product="Xaa at position 25 is
                Cha"

(ix) FEATURE:
            (A) NAME/KEY: Modified-site
            (B) LOCATION: 26
            (D) OTHER INFORMATION: /product="Glu at position 26 is
                D-Glu OH"

(xi) SEQUENCE DESCRIPTION: SEQ ID NO:2:

Ile Arg Phe Thr Asp Ala Gly Ala Pro Glu Ser His Phe Gly Gly Asp
1               5                   10                  15

Tyr Glu Glu Ile Pro Xaa Xaa Tyr Xaa Glu
            20              25

(2) INFORMATION FOR SEQ ID NO:3:

(i) SEQUENCE CHARACTERISTICS:
            (A) LENGTH: 26 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product="Xaa in position 1 is
                Chg"

(ix) FEATURE:
            (A) NAME/KEY: Modified-site
            (B) LOCATION: 2
            (D) OTHER INFORMATION: /product="Xaa in position 2 is
                2-Nal"

(ix) FEATURE:
            (A) NAME/KEY: Modified-site
            (B) LOCATION: 6
            (D) OTHER INFORMATION: /product="Ala in position 6 is
                D-Ala"

(ix) FEATURE:
            (A) NAME/KEY: Modified-site
            (B) LOCATION: 8
            (D) OTHER INFORMATION: /product="Ala in position 8 is
                beta-Ala"

(ix) FEATURE:
            (A) NAME/KEY: Modified-site
            (B) LOCATION: 13
            (D) OTHER INFORMATION: /product="Phe in position 13 is
                b-Phe"

(ix) FEATURE:
            (A) NAME/KEY: Modified-site (B) LOCATION: 22
(D) OTHER INFORMATION: /product="Xaa in position 22 is Aib"

(ix) FEATURE:
(A) NAME/KEY: Modified-site
(B) LOCATION: 23
(D) OTHER INFORMATION: /product="Xaa in position 23 is Aib"

(ix) FEATURE:
(A) NAME/KEY: Modified-site
(B) LOCATION: 25
(D) OTHER INFORMATION: /product="Xaa in position 25 is Cha"

(ix) FEATURE:
(A) NAME/KEY: Modified-site
(B) LOCATION: 26
(D) OTHER INFORMATION: /product="Glu in position 26 is D-Glu OH"

(xi) SEQUENCE DESCRIPTION: SEQ ID NO:3:

Xaa Arg Xaa Thr Asp Ala Gly Ala Pro Glu Ser His Phe Gly Gly Asp
1               5                   10                  15

Tyr Glu Glu Ile Pro Xaa Xaa Tyr Xaa Glu
        20                  25

(2) INFORMATION FOR SEQ ID NO:4:

(i) SEQUENCE CHARACTERISTICS:
(A) LENGTH: 26 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /product="Xaa in position 1 is Cha"

(ix) FEATURE:
(A) NAME/KEY: Modified-site
(B) LOCATION: 3
(D) OTHER INFORMATION: /product="Xaa in position 3 is 2-Nal"

(ix) FEATURE:
(A) NAME/KEY: Modified-site
(B) LOCATION: 6
(D) OTHER INFORMATION: /product="Ala in position 6 is D-Ala"

(ix) FEATURE:
(A) NAME/KEY: Modified-site
(B) LOCATION: 8
(D) OTHER INFORMATION: /product="Ala in position 8 is beta-Ala"

(ix) FEATURE:
(A) NAME/KEY: Modified-site
(B) LOCATION: 13
(D) OTHER INFORMATION: /product="Phe in position 13 is h-Phe"

(ix) FEATURE:
(A) NAME/KEY: Modified-site
(B) LOCATION: 22
(D) OTHER INFORMATION: /product="Xaa in position 22 is Aib"

(ix) FEATURE:
(A) NAME/KEY: Modified-site
(B) LOCATION: 23

(D) OTHER INFORMATION: /product="Xaa in position 23 is
                  Aib"

(ix) FEATURE:
              (A) NAME/KEY: Modified-site
              (B) LOCATION: 25
              (D) OTHER INFORMATION: /product="Xaa in position 25 is
                  Cha"

(ix) FEATURE:
              (A) NAME/KEY: Modified-site
              (B) LOCATION: 26
              (D) OTHER INFORMATION: /product="Glu in position 26 is
                  D-Glu OH"

(xi) SEQUENCE DESCRIPTION: SEQ ID NO:4:

Xaa  Val  Xaa  Thr  Asp  Ala  Gly  Ala  Pro  Glu  Ser  His  Phe  Gly  Gly  Asp
 1              5                             10                            15

Tyr  Glu  Glu  Ile  Pro  Xaa  Xaa  Tyr  Xaa  Glu
           20                            25

(2) INFORMATION FOR SEQ ID NO:5:

(i) SEQUENCE CHARACTERISTICS:
              (A) LENGTH: 26 amino acids
              (B) TYPE: amino acid
              (C) STRANDEDNESS: single
              (D) TOPOLOGY: linear (ii) MOLECULE TYPE: peptide (ix) FEATURE:
              (A) NAME/KEY: Modified-site
              (B) LOCATION: 6
              (D) OTHER INFORMATION: /product="Ala in position 6 is
                  D-Ala"

(ix) FEATURE:
              (A) NAME/KEY: Modified-site
              (B) LOCATION: 8
              (D) OTHER INFORMATION: /product="Ala in position 8 is
                  beta-Ala"

(ix) FEATURE:
              (A) NAME/KEY: Modified-site
              (B) LOCATION: 13
              (D) OTHER INFORMATION: /product="Phe in position 13 is
                  h-Phe"

(ix) FEATURE:
              (A) NAME/KEY: Modified-site
              (B) LOCATION: 22
              (D) OTHER INFORMATION: /product="Xaa in position 22 is
                  Aib"

(ix) FEATURE:
              (A) NAME/KEY: Modified-site
              (B) LOCATION: 23
              (D) OTHER INFORMATION: /product="Xaa in position 23 is
                  Aib"

(ix) FEATURE:
              (A) NAME/KEY: Modified-site
              (B) LOCATION: 24
              (D) OTHER INFORMATION: /product="Phe in position 24 is
                  PO4H2-Phe"

(ix) FEATURE:
              (A) NAME/KEY: Modified-site
              (B) LOCATION: 25
              (D) OTHER INFORMATION: /product="Xaa in position 25 is
                  Cha"

(ix) FEATURE:
              (A) NAME/KEY: Modified-site
              (B) LOCATION: 26
              (D) OTHER INFORMATION: /product="Glu in position 26 is D-Glu OH"

( x i ) SEQUENCE DESCRIPTION: SEQ ID NO:5:

```
Ile Arg Phe Thr Asp Ala Gly Ala Pro Glu Ser His Phe Gly Gly Asp
 1               5                  10                      15

Tyr Glu Glu Ile Pro Xaa Xaa Phe Xaa Glu
            20              25
```

THROMBIN INHIBITORS, THE PREPARATION THEREOF AND THE USE THEREOF FOR THERAPEUTICAL, PROPHYLACTIC AND DIAGNOSTIC APPLICATIONS

The present invention relates to thrombin inhibitors, the preparation thereof and the use thereof for therapeutical, prophylactic and diagnostic applications.

Thrombin is a serin-protease involved in various important physiological functions [Fenton, J. W. (1981) Annal. N.Y. Acad. Sci., 370, 468–495; Bar Shavit, R. and Wilner, G. D. (1986) Int. Rev. Exp. Pathol., 29, 213–241].

Besides playing a role in blood coagulation, thrombin also has other activities, among which a strong mitogenic signal with fibroblasts in vitro, and it also exerts a chemotactic effect on monocytes (Bar Shavit).

Thrombin stimulates the formation of cGMP in neuroblastoma cells [Snider, R. M. et al. (1984), J. Biol. Chem., 259, 9078–9081; Snider, R. M. (1986), Ann. N.Y. Acad. Sci., 485, 310–313]: it is involved in the control of neuronal differentiation [Gurwitz D. and Cunningham, D. D. (1988), Proc. Natl. Acad. Sci., 85, 3440–3444].

Thrombin seems to also have a role in promoting cancer, due to the capability of fibrin, which is its digestion product, to act as a substrate for tumour growth [Falanga A. et al. (1985) Biochemistry, 24, 5558–67; Gordon, S. G. et al. (1985), Blood, 66, 1261–65; Falanga A. et al. (1988), Blood, 71, 870–75].

Many pathologies being a high risk for health, such as cardiac infarction, thrombosis, peripheral arteries occlusions, and the like, require a regulation of thrombin activity.

The physiological inhibitor of thrombin in blood is antithrombin III, but thrombin is poorly inhibited by it [Rosenberg, R. D. (1977), Fed. Proc., Fed. Am. Soc. Exp. Biol., 36, 10–18]. Heparin increases thrombin activation rate by at least 3–4 magnitudes [Olson, S. T. and Shore, J. D. (1982), J. Biol. Chem., 257, 14891–14895], therefore it is commonly used as a therapeutical agent, e.g. in venous thromboembolism, in which thrombin activity is responsible for the development or the expansion of a thrombus.

However, the use of heparin has some drawbacks: it is ineffective in patients lacking antithrombin III and it has a short half-life in blood; it fails to interrupt platelet-mediated arterial thrombosis or the formation of the hemostatic plug [Salzman, E. W. et al. (1980), J. Clin. Invest., 65, 64–73; Hanson, R. S. and Harker, L. A. (1988), Proc. Natl. Acad. Sci., USA, 85, 3184–3188]. Due to these and other drawbacks, a search for different compounds useful for a fast inactivation of thrombin has been required.

Hirudin, a polypeptide of molecular weight 6950 excreted by the salivary glands of Hirudo medicinalis, belongs to a family of polypeptides containing about 65 single chain amino acids (a.a.) and it is a strong specific thrombin inhibitor [Chang, J. Y. (1983), FEBS, 164 (2), 307–313; Konno, S., et al., G. B. 1988, Arch. Bioch. Biophys. 267, 158–166; Fenton J. W. et al. (1988), Biochemistry, 27, 7106–7112; Stone, S. R. et al. (1986), Biochemistry, 25, 4622–4628]. Hirudin binds to thrombin ($K_i = 6.3 \times 10^{-11}$M) forming a non covalent complex 1:1; such an interaction occurs at a different site from the enzyme catalytic site, even though hirudin additionally also binds to the active site. Therefore, in hirudin itself, three different domains can be evidenced: i) the N-terminal segment penetrating into thrombin catalytic site; ii) the C-terminal segment, of about 18 residues, which binds in a mainly cationic groove of thrombin; iii) the central nucleus (residues 5–48) acting as a spacer of the two N- and C-terminal domains.

Hirudin has successfully been used as an anticoagulant and antithrombotic agent. Contrary to heparin, hirudin require s no presence of endogenous cofactors such as antithrombin III and it is not bound or inactivated by platelet factors or by other substances having antiheparin effects. Hirudin differs from heparin in that it causes no bleeding side-effects.

Notwithstanding said advantages and even though hirudin is nowadays prepared by recombinant DNA techniques [Markwardt, F. (1991), Haemostasis, 21, Suppl. 1, 11–26], the clinical use of hirudin is restricted mainly since the substance is not available in sufficient amounts for therapeutical purposes.

Therefore a number of researchers are involved efforts to synthesize hirudin peptide fragments which are easier and less expensive to prepare and have an antithrombotic activity similar or even higher than that of hirudin.

Compounds inhibiting thrombin are known in literature and among them particularly interesting are hirudin peptide fragments [EP-468448; WO-9119734; GB-2242681; EP-443598; EP-443429; EP-421367; WO-9101328; WO-9101142; EP-372670; EP-372503; EP-364942; EP-341607; 9049 U.S. Pat. No. 4,971,953; EP-333356; EP-291982; EP-276014; WO-9102750; J. M. Maraganore, et al., Biochemistry, (1990), 29, 70957101; J. M. Maraganore, et al., J. Biol. Chem., (1989), 264, 86928698; M. Scharf, et al., FEBS, (1989), 255, 105110), W. J. Hoekstra, et al., Tetrahedron, (1992), 48, 207318; P. J. Braun, et al., Biochemistry, (1988), 27, 65176522; A. Wallace, et al., Biochemistry, (1989), 28, 1007910084; J. Dodt, et al., FEB, (1988), 229, 8790; T. J. Owen, et al., J. Medicinal Chem., (1988), 10091011; J. L. Krstenansky, et al., J. Medicinal Chem., (1987), 16881691; J. B. Lazar, et al., J. Biol. Chem., (1991), 266, 685688; S. Dennis, et al., Eur. J. Biochem., (1990), 188, 6166; V. Steiner, et al., Biochemistry, (1992), 31, 22942298; A. Betz, et al., Biochemistry, (1992), 31, 45574562, S. J. Di Maio, et al., J. Biol. Chem., (1990), 265, 2169821703].

Among them, two class of compounds are particularly relevant: i) those reproducing the C-terminal domain of hirudin (48–65 or smaller sizes) which therefore bind only to the non-catalytic site of thrombin; ii) those which, analogously to hirudin, contain an N-terminal domain penetrating into the catalytic site, a spacer and a domain corresponding to the C-terminal segment of hirudin which binds to the non-catalytic site. The latter compounds penetrate into the catalytic site of thrombin thereby forming a β-strand which is antiparallel with the $Ser^{214}$-$Gly^{216}$ residues such as in the case of other serineprotease-inhibitor complexes and therefore they can be subjected to hydrolysis [E. SkrzypczakJankun, et al., J. Mol. Biol. (1991), 221, 13791393; I. W. Witting, et al., Biochem. J. (1992), 283, 737–743].

The present invention relates to novel hirudin analogues, for which the name "hirunorms" is proposed, with a chemical composition different from the up to now developed ones. Said compounds, showing an overall biological activity higher than that of already known products, have the following general formula (I):

G1-G2-G3-G4-G5-G6-G7-G8-G9-F1-F2-F3-F4-F5-F6E1-E2-E3-E4-E5-E6-E7-E8-E9-E10 wherein:

G1 - Ile, Val, Leu, Cha, Chg, aIle, Nle, Pro, Pip, Phe, Tyr, Trp, Pgl, 1-Nal, 2-Nal, Met
G2 - Arg, Val, L-Pap, L-Map, Ala, Ile, Leu, Lys, Orn, Thr, aThr, aIle, Ser
G3 - 2-Nal, Phe, 1-Nal, Trp, Tyr, Cha, Pgl, Chg
G4 - Thr, Ser, Asn, Gln, His, aThr
G5 - Asp, Glu
G6 - D-Ala, Aib, Gly, Ac$_6$c, Ac$_5$c
G7 - ε-Aca, δ-Ava, β-Ala-β-Ala, β-Ala-β-Ac$_5$c, β-Ala-β-Ac$_6$c, β-Ala—Gly, β-Ala-Gaba, Gly-β-Ala, Gly—Gly, Gly-Gaba, Gly-δ-Ava, Gaba-Gly, Gaba-β-Ala, δ-Ava-Gly, Gly—Gly—Gly
G8 - Pro, Ala, Gly, Ac$_6$c, Ac$_5$c
G9 - Glu
F1 - Ser, Asn, Gln, Thr, aThr, His, h-Ser, h-Phe
F2 - His
F3 - h-Phe, Leu, Asp, Asn, Gly, Nle, Ile, aIle, Val, Cha, Chg, Phe, Tyr, Pgl, Trp, 1-Nal, 2-Nal, Met, Deg, Dpg
F4 - Gly, Asp, Asn
F5 - Gly, Ala, D-Ala, Deg, Dpg
F6 - Asp
E1 - Tyr, Phe, Trp, Cha, His, Pgl, 1-Nal, 2-Nal, Chg
E2 - Glu
E3 - Glu, Pro, Sar, Hyp, Δ-Pro, thioproline, Pip, Azt
E4 - Ile, Chg, Cha,
E5 - Pro, Sar, Hyp, Δ-Pro, thioproline, Pip, Azt
E6 - Aib, Ala, Ac$_6$c, Ac$_5$c, Ac$_4$c, Ac$_3$c, cis or trans Δ-Glu, (S) or (R)-αMe—Glu, Asp, Glu
E7 - Aib, Ala, Ac$_6$c, Ac$_5$c, Ac$_4$c, Ac$_3$c, cis or trans Δ-Glu, (S) or (R)-αMe—Glu, Asp, Glu
E8 - Tyr, cis or trans Δ-Tyr, (S) or (R)-αMe—Tyr, Phe, Aib, Ala, para or meta NO$_2$—Phe, para or meta SO$_3$H—Phe, para or meta PO$_3$H$_2$—Phe, para or meta PO$_4$H$_2$—Phe, para or meta SO$_4$H—Phe, meta SO$_3$H—Tyr, meta PO$_3$H$_2$—Tyr, para or meta CH$_2$PO$_3$H$_2$—Phe, para or meta CH$_2$SO$_3$H—Phe, para or meta CH$_2$COOH—Phe, para or meta CO$_3$H—Phe
E9 - Cha, Leu, cis or trans Δ-Leu, (S) or (R) αMe—Leu
E10 - D-Glu, Glu, β-Ala, Asp, D-Asp, Gly, Ala, Gln, Gla Particularly preferred are:

a) compounds of general formula (I) wherein:

G1 = Ile or Val or Leu or Cha or Chg or aIle or Nle or Pro or Phe or Tyr or Trp or Pgl or 1-Nal or 2-Nal or Met; G2 = Arg or L—Pap or L—Map or Val or Thr or Ile or Ala or Ser; G3 = 2-Nal or Phe or 1-Nal or Trp or Tyr; G4 = Thr; G5 = Asp; G6 = D—Ala; G7 = Gly-β-Ala or β-Ala-β-Ala; G8 = Pro; G9 = Glu, F1 = Ser or Asn or h-Ser or h-Phe; F2 = His; F3 = Nle or Cha or Met or h-Phe; F4 = Gly; F5 = Gly; F6 = Asp; E1 = Tyr or Phe; E2 = Glu; E3 = Glu or Pro; E4 = Ile; E5 = Pro; E6 = Aib; E7 = Aib; E8 = Tyr or PO$_4$H$_2$—Phe; E9 = Cha or Leu; E10 = D—Glu or Glu;

b) compounds of formula (I) wherein:

G1 = Chg or Ile or Val or aIle or Nle or Phe or Tyr or Trp or Pgl or 1-Nal or 2-Nal; G2 = Arg or Val; G3 = 2-Nal or Phe or 1-Nal; G4 = Thr; G5 = Asp; G6 = D—Ala; G7 = Gly-β-Ala; G8 = Pro; G9 = Glu; F1 = Ser; F2 = His; F3 = Nle or h-Phe; F4 = Gly; F5 = Gly; F6 = Asp; E1 = Tyr or Phe; E2 = Glu; E3 = Glu or Pro; E4 = Ile; E5 = Pro; E6 = Aib; E7 = Tyr or PO$_4$H$_2$—Phe; E9 = Cha or Leu; E10 = D—Glu or Glu.

In the following, the abbreviations used in the disclosure are reported: Orn=ornithine, Gly=glycine, Ala=alanine, Val=valine, Leu=leucine, Δ-Leu=dehydroleucine, αMe-Leu=α-methylleucine, Ile=isoleucine, Pro=proline, Phe=phenylalanine, Trp=tryptophan, Met=methionine, Ser=serine, Thr=threonine, Tyr=tyrosine, Δ-Tyr=α-β-dehydrotyrosine, αMe-Tyr=methyltyrosine, Asn=asparagine, Gln=glutamine, Asp=aspartic acid, Lys=lysine, His=histidine, Glu=glutamic acid, Arg=arginine, Nle=norleucine, Hyp=hydroxyproline, Δ-Pro=dehydroproline, Δ-Glu=α-β-dehydroglutamic acid, αMe-Glu=α-methylglutamic acid, Pgl=phenylglycine, 1-Nal=β-1-naphthylalanine, 2-Nal=β-2-naphthylalanine, Cha=cyclohexylalanine, aIle=allo-isoleucine, Chg=cyclohexylglycine, h-Phe=omophenylalanine, h-Set=omoserine, Sar=sarcosine, Pip=pipecolic acid, Azt=azetidinic acid, gla=γ-carboxyglutamic, Pap=para-amidinophenylalanine, Map=meta-amidino-phenylalanine, Deg=diethylglycine, Dpg=dipropylglycine, aThr=allo-threonine, Aba=α-amino-n-butyric acid, Pba=αaminophenylbutyric acid, Aib=α-aminoisobutyric acid (α-methyl-alanine), Dap= 2,3 diaminopropionic acid, Dab=2,4 diaminobutyric acid, Gaba=γ-aminobutyric acid, εAca=ε-aminocaproic acid, δ-Ava=δ-aminovaleric acid, β-Ala=β-alanine, Ac$_3$c=α-aminocyclopropanecarboxylic acid, Ac$_4$c=α-aminocyclobutanecarboxylic acid, Ac$_5$c=α-aminocyclopentanecarboxylic acid, Ac$_6$c=α-aminocyclohexanecarboxylic acid, β-Ac$_5$c=β-aminocyclopentanecarboxylic acid, β-Ac$_6$c=β-aminocyclohexanecarboxylic acid, NO$_2$-Phe=nitrophenylalanine, SO$_3$H-Phe=phenylalanine sulfonate, PO$_3$H$_2$-phe=phenylalanine phosphonate, PO$_4$H$_2$-Phe=phenylalanine phosphate, SO$_4$H-phe=phenylalanine sulfate, SO$_3$H-Tyr=tyrosine-m-sulfonate, PO$_3$H$_2$-Tyr=tyrosine-m-phosphonate, CH$_2$PO$_3$H$_2$-phe=phenylalanine methylphosphonate, CH$_2$SO$_3$H-Phe=phenylalanine methylsulfonate, CH$_2$COOH-Phe=phenylalanine acetate, CO$_3$H-Phe=phenylalanine carbonate, Boc=tert-butyloxycarbonyl, Fmoc=fluorenylmethoxycarbonyl, Bzl= benzyl ester, PAM=phenylacetoxymethyl, TFA= trifluoroacetic acid, DCM=dichloromethane, DIEA -diisopropylethylamine, DMF=dimethylformamide, OBzl= benzyl ether, PyBop=benzotriazole-1-yl-oxy-tris-pyrrolidino-phosphonium-hexafluorophosphate, DCC= dicyclohexylcarbodiimmide, DCU=dicyclohexylurea, Bom=π-benzyloxymethyl, Tos=tosyl, BSA=bovine seroalbumin.

As far as the definitions of the different amino acids are concerned, reference is made to The Biochemical Journal 219, No. 2, 345-373 (1984).

The peptides of the present invention contain a number of charged groups on the amino acids side chains and of course they have to be neutralized with suitable counter-ions. Since any positively charged chemical group can be a potential counter-ion, only the pharmaceutically acceptable ones will be used, i.e. those cations which are non toxic at the used doses and do not have in their turn any undesired actions. Non-limiting examples of counter-ions are: alkali or alkaline-earth metal ions, or $Al^{3+}$, primary, secondary and tertiary organic amines.

The peptides of the present invention can of course be administered also in the acidic form by adding inorganic or organic acids, such as HCl, HBr, $H_2SO_4$, $H_3PO_4$ or acetic, piruvic, succinic, glutaric, fumaric, malic, tartaric, citric, ascorbic, maleic acid.

The peptides of the present invention can also be prepared by the various techniques reported in literature, see e.g. Schroeder et al. "The Peptides" vol. 1, Academic Press, 1965; Bodanszky et al. "Peptide Synthesis Interscience Publisher, 1966; Barany & Merrifield, "The peptides; Analysis, Synthesis, Biology", 2, Chapter 1, Academic Press, 1980. Said techniques include peptide synthesis in solid phase, peptide synthesis in solution, organic chemistry synthetic methods, or any combination thereof. The selected synthesis scheme will depend of course on the composition of the particular molecule. Preferably, the claimed molecules being entirely on a peptide basis, synthetic methods based on suitable combinations of solid phase technique and conventional solution methods are used, which involve low costs particularly on industrial scale.

The synthesis of peptides containing sulfonated, sulfated, phosphated or phosphonated tyrosines, or containing methylphosphonated or methylsulfonated phenylalanines, can be carried out according to one of the methods described in literature [J. M. Lacombe et al., Int. J. Peptide Protein Res., (1990), 36, 275–280; C. Garbay-Jaureguiberry et al., Int. J. Peptides Protein Res., (1992), 39, 523–527].

Preferably, the synthesis of the peptides containing aromatic amino acids substituted with anion groups at one of the meta or para positions of the ring, can be carried out by means of two alternative procedures: i) "Global Approach"; ii) "Building Block Strategy".

The first procedure involves the complete synthesis, both with Boc and Fmoc chemistry, of the desired peptide, on which the residues to be phosphorylated with the side chains unprotected are introduced. The phosphorylation reaction is then carried out using different reagents and a variety of phosphite-protecting groups: (isopropyl)$_2$N-P(OR)$_2$ with R-ethyl, benzyl, methyl, tert-butyl. The subsequent oxidation of the phosphite by tert-butyl peroxide and the cleavage from the resin yields the desired phosphopeptide.

The second strategy makes use of the previously phosphated tyrosine, which can be introduced by means of the solid phase technique, with both Boc and Fmoc chemistry.

The compounds of the present invention (hirunorms) contain three domains (as the hirudin natural molecule): 1) a C-terminal domain; 2) a spacer arm; 3) an N-terminal domain. It should be pointed out that, for the used structural solutions, the hirunorms reproduce the action mechanism of hirudin.

Hirudin interacts with thrombin on two different regions: a groove different from the catalytic site, being mainly cationic, and the catalytic site itself. The N-terminal segment of hirudin penetrates into this site, thereby forming a β-strand parallel with the $Ser^{214}Gly^{216}$ residue, and therefore it cannot be hydrolyzed by thrombin itself. The C-terminal segment interacts with a number of amino acid residues in the groove far from the catalytic site. Hirudin central nucleus has poor interactions with thrombin itself, but it plays an important role in the parallel location of the N-terminal segment of hirudin in the catalytic site [T. J. Rydel, A. Tulinsky, W. Bode, R. Huber, J. Mol. Biol., (1991), 221, 583601].

A schematic comparative analysis of the structural, functional and biological characteristic of the compounds of the invention compared with hirudin is reported below.

1) The compounds of the invention have a molecular weight, at least the half of that of hirudin, therefore requiring synthetic procedures easier on industrial scale.

2) The N-terminal moiety has a composition similar to the one of hirudin and it has access to the catalytic site from the same direction, thus it is not subjected to the amidolytic action of thrombin itself.

3) The linker moiety is at least 3 times smaller than hirudin and the optimization of the interaction, related to the use of particular non protein amino acids, makes more specific the interaction with thrombin.

4) In the C-terminal moiety, more than 40% of the amino acidic residues are different from those of hirudin and they contribute in optimizing the interactions between this peptide segment and the cationic groove on thrombin surface.

Hereinafter, the peptide sequences of the examples of the invention are reported.

a) hirudin; b) hirunorm-I; c) hirunorm-II; d) hirunorm-III; e) hirunorm IV; f) hirunorm V.

A) The numeration refers to hirudin amino acid residues; residues 6 to 47 are not reported. I) N-Terminal moiety; II) linker moiety; III) C-terminal moiety. The amino acid substitutions never used before to prepare hirudin-related peptide analogues are indicated in bold-type.

Tyr(-) means phenylalanine phosphate.

| A | a | b | c | d | e | f |
|---|---|---|---|---|---|---|
| I) 1 | Ile | Ile | Ile | Ile | Chg | Chg |
| 2 | Val | Arg | Arg | Arg | Arg | Val |
| 3 | Tyr | Tyr | Phe | Phe | 2-Nal | 2-Nal |
| II) 4 | Thr | Thr | Thr | Thr | Thr | Thr |
| 5 | Asp | Asp | Asp | Asp | Asp | Asp |
| * * | | D-Ala | D-Ala | D-Ala | D-Ala | D-Ala |
| * * | | β-Ala | Gly | Gly | Gly | Gly |
| * * | | β-Ala | β-Ala | β-Ala | β-Ala | β-Ala |
| 48 | Pro | Pro | Pro | Pro | Pro | Pro |
| 49 | Glu | Glu | Glu | Glu | Glu | Glu |
| 50 | Ser | Asn | Ser | Ser | Ser | Ser |
| 51 | His | His | His | His | His | His |
| 52 | Asn | Asn | h-Phe | h-Phe | h-Phe | h-Phe |
| 53 | Asx | Asn | Gly | Gly | Gly | Gly |
| 54 | Gly | Gly | Gly | Gly | Gly | Gly |
| 55 | Asp | Asp | Asp | Asp | Asp | Asp |
| 56 | Phe | Phe | Tyr | Tyr | Tyr | Tyr |
| III) 57 | Glu | Glu | Glu | Glu | Glu | Glu |
| 58 | Glu | Glu | Glu | Glu | Glu | Glu |
| 59 | Ile | Ile | Ile | Ile | Ile | Ile |
| 60 | Pro | Pro | Pro | Pro | Pro | Pro |
| 61 | Glu | Aib | Aib | Aib | Aib | Aib |
| 62 | Glu | Aib | Aib | Aib | Aib | Aib |
| 63 | Tyr | Tyr | Tyr | Tyr(-) | Tyr | Tyr |
| 64 | Leu | Leu | Cha | Cha | Cha | Cha |
| 65 | Gln | Glu | D-Glu | D-Glu | D-Glu | D-Glu |

In conclusion, the claimed peptides have the following characteristics:

1) They have been designed to function analogously to hirudin and differently from the other peptide inhibitors analogues of hirudin.

2) They show activities higher than hirudin.

3) They are synthetically simpler than hirudin.

However, it is necessary to stress how, due to the particular kind of interaction of the claimed molecules with thrombin, other amino acid substitutions, non specifically envisaged but within the peculiar molecular structure of hirunorms, can be carried out to improve the biological strength.

Accordingly, owing to the structural and functional characteristics thereof, the peptides of the invention proved to be stronger specific inhibitors of thrombin.

The efficacy of hirunorms was evaluated in vitro by measuring APTT (Activated Partial Thromboplastin Time), PT (Prothrombin Time) and TT (Thrombin Time) in the presence of increasing amounts of the product on healthy donors' plasma and compared with normal values and values obtained with hirudin. The efficacy of the claimed molecules in inhibiting platelet aggregation was evaluated also in vitro using PRP (platelet-rich plasma of healthy donors) or PPP (platelet poor plasma).

The resistance of the compounds of the present invention versus plasmatic proteases was evaluated in vitro in two groups of tests. In the first one, the resistance to proteolysis of thrombin itself was tested incubating the claimed compounds in the presence of thrombin and analysing the mixture at different times. In the second one, the claimed compounds were incubated in plasma of healthy volunteers and, after filtration of the plasma proteins, the supernatants were analyzed by HPLC and capillary electrophoresis.

Moreover, the efficacy of the products of the present invention was also evaluated determining the inhibition constants $K_i$ versus thrombin, using chromogenic substrates.

The anticoagulant dose of a peptide of the invention can vary from 0.05 mg/Kg to 250 mg/Kg patient body weight per day, depending on the patient, the severity of the thrombotic condition and the selected peptide. The term "patient" as herein used includes mammals, such as primates, man included, ovines, bovines, horses, cats, dogs, pigs, rats, mice. The suitable dose can be determined easily, preferably the treatment should envisage up to 4 daily doses which can vary from 1 to 100 mg of active compound per dose. These compounds have a strong anticoagulant activity, therefore they can be used in the treatment and prevention of a wide variety of thrombotic conditions, particularly cerebro-vascular and coronary arterial diseases, more generally of all of those pathologies in which an anticoagulant action is beneficial. The compounds can be used in combinations, compositions and methods for the treatment of cardiac infarction, pulmonary embolism, venous thrombosis, peripheral arteries occlusion, restenosis following arterial damage or invasive cardiologic surgery.

They can also be used in the therapy of thrombotic pathologies in combination with a thrombolytic agent to decrease the reperfusion time and prevent any reocclusions. In such a way, the dosage of the used thrombolytic agent can be decreased, thus preventing the involved side-effects, such as the risk of bleeding.

The products of the invention can be coated in layered on the surface of invasive prostheses such as artificial valves, vascular grafts, catheters and the like, to prevent any formations of clots or aggregation and platelet activation in patients carrying said prostheses.

The compounds of the present invention can also be used in preventing venous and arterial thrombosis and disseminated intravascular coagulation. Moreover, they can be used in the prophylaxis of arterial thrombosis, particularly in cardiosurgery, to prevent coronary by-pass occlusion and thrombotic reocclusion following transluminal percutaneous coronary angioplasty, or after thrombolysis in venous and arterial vessels. They can also be used in extracorporeal circulation, particularly in hemodialysis.

The compounds of the invention can, besides in the prevention of vascular pathologies, be used in the prophylaxis of inflammatory responses, tumour pathologies and neuro-vegetative disorders, therefore the use thereof is important in the treatment of chronic or acute atherosclerosis, oedema and inflammations, tumours and metastases, and neurodegenerative diseases such as Parkinson's disease and Alzheimer disease.

The compounds of the present invention are suitable for the therapeutical administration to higher animals and man through the parenteral, subcutaneous, topical or nasal routes, attaining pharmacological effects according to the above described properties. Suitable forms for the oral administration are aqueous or oily solutions or suspension, emulsions, syrups, elixirs or freeze-dried forms. Topical administration can be effected by means of preparations such as aqueous gels, oily suspensions or emulsions. The doses of active ingredient in said compositions can range from 0.1 to 10 mg/kg body weight. The compounds of the invention can also be administered in form of depot injection or implant preparation, which can be formulated to allow a substantial release of the active ingredient. The active ingredient can be compressed in tablets or small cylinders and subcutaneously or intramuscularly implanted in form of depot injections or implants. The implants can consist of inert materials, such as biodegradable polymers or synthetic silicons.

The compounds of the invention can have a number of applications in diagnostics. They are indeed a versatile tool to selectively prevent or interrupt thrombin action in biochemical and diagnostic systems.

The compounds can be used in kinetics studies of the fibrin-peptide release thrombin-catalyzed, of the fibrin structure and of the interaction between fibrinogen fragments and fibrin mono- and oligomers.

The compounds can be used in studies of thrombin binding to cell receptors of platelet, endothelial cells, fibroblasts and cancer cells.

The compounds can be added in an excess to blood, plasma or cell mixtures to prevent thrombin action immediately after its production; they can be used to titre a thrombin specific amount.

The compounds can be used to discriminate the activity of thrombin, of the precursors and cofactors thereof, and the activities of other plasma proteases.

For the specific applications in diagnostics, the peptides of the invention can be, for example, the essential constituent of a kit for the determination of the concentration of factor IXa, of factor Xa of thrombin or of mixtures thereof in a biological sample. The peptides of the invention can also be labelled with a radioisotope for ex vivo imaging of fibrin or platelet thrombi.

The following examples further illustrate the invention.

EXAMPLE 1

Preparation of the compound hirunorm-I having structure

Ile—Arg—Tyr—Thr—Asp—D—Ala-β-Ala-β-Ala—Pro—Glu—Asn—His—Asn—Asn—Gly—Asp—Phe—Glu—Glu—Ile—Pro—Aib—Aib—Tyr—Leu—Glu—OH [compounds of formula (I) wherein G1 = Ile, G2 = Arg, G3 = Tyr, G4 = Thr, G5 = Asp, G6 = D—Ala, G7 = β-Ala-β-Ala, G8 = Pro, G9 = Glu, F1 = Asn, F2 = His, F3 = Asn, F4 = Asn, F5 = Gly, F6 = Asp, E1 = Phe, E2 = Glu, E3 = Glu, E4 = Ile, E5 = Pro, E6 = Aib, E7 = Aib, E8 = Tyr, E9 = Leu, E10 = Glu], corresponding to Sequence Id no. 1.

An automatic peptide synthesizer was used for the preparation, starting from 0.714 g of Boc-Glu(γBzl)-OCH$_2$-PAM resin (0.70 meq/g), equivalent to 0.5 mmol of amino groups. The various amino acids, suitably protected, are then reacted in the correct order. The acylation time is 1 hour. For the acylation with Boc-Aib-OH, the reaction mixture is added with PyBop (2 mmol) in DMF and coupling is repeated for 2 hours. All the other amino acids are coupled as symmetric anhydrides, dissolving 2 mmol of amino acid in 5 ml of DCM, the solution is cooled to 0° C. and 1 ml of a 0.5M DCC solution in DCM is added ; after 15 min DCU is filtered and the resulting solution is added to the deprotected resin. The dry resin is placed into a teflon reactor with 1 ml of anisole; the mixture is cooled to −50° C. and 10 ml of hydrofluoric acid are distilled therein, then the mixture is stirred for 1 h in an ice bath. The product is dried, washed with ethyl ether (2×15 ml) and extracted with 50% acetic acid (3×15 ml), filtered through a porous filter to remove the exhausted resin. The resulting product is diluted with water and freeze-dried. The peptide is finally purified by reverse phase chromatography and characterized by analytic HPLC with a Vydac C18 0.46×25 cm column, with a linear gradient in acetonitrile containing 0.1% (v/v) of trifluoroacetic acid (phase B) against 0.1% (v/v) aqueous trifluoroacetic acid (Phase A), from 5 to 70% in B in 35 min at flow rate of 1 ml/min, with UV detector at 210 nm. Retention time (Rt)= 24.8 min; chromatographic purity>99%.

EXAMPLE 2

Analogously, the following peptides are prepared:

hirunorm-II of structure

Ile—Arg—Phe—Thr—Asp—D—Ala—Gly-β-Ala—Pro—Glu—Ser—His—h-Phe—Gly—Gly—Asp—Tyr—Glu—Glu—Ile—Pro—Aib—Aib—Tyr—Cha—D—Glu—OH [compounds of formula (I) wherein G1 = Ile, G2 = Arg, G3 = Phe, G4 = Thr, G5 = Asp, G6 = D—Ala, G7 = Gly-β-Ala, G8 = Pro, G9 = Glu, F1 = Ser, F2 = His, F3 = h-Phe, F4 = Gly, F5 = Gly, F6 = Asp, E1 = Tyr, E2 = Glu, E3 = Glu, E4 = Ile, E5 = Pro, E6 = Aib, E7 = Aib, E8 = Tyr, E9 = Cha, E10 = D—Glu]. Rt −28.7 min (Sequence Id no. 2).

hirunorm-IV of structure

Chg—Arg-2-Nal—Thr—Asp—D—Ala—Gly-β-Ala—Pro—Glu—Ser—His-h-Phe—Gly—Gly—Asp—Tyr—Glu—Glu—Ile—Pro—Aib—Aib—Tyr—Cha—D—Glu—OH (compounds of formula (I) wherein G1 = Chg, G2 = Arg, G3 = 2-Nal, G4 = Thr, G5 = Asp, G6 = D—Ala, G7 = Gly-β-Ala, G8 = Pro, G9 = Glu, F1 = Ser, F2 = His, F3 = h-Phe, F4 = Gly, F5 = Gly, F6 = Asp, E1 = Tyr, E2 = Glu, E3 = Glu, E4 = Ile, E5 = Pro, E6 = Aib, E7 = Aib, E8 = Tyr, E9 = Cha, E10 = D—Glu]. Rt = 21.1 min (Sequence Id no. 3).

hirunorm-V of structure

CHg—Val-2-Nal—Thr—Asp—D—Ala—Gly-β-Ala—Pro—Glu—Ser—His-h-Phe—Gly—Gly—Asp—Tyr—Glu—Glu—Ile—Pro—Aib—Aib—Tyr—Cha—D—Glu—OH [compounds of formula (I) wherein G1 = Chg, G2 = Val, G3 = 2-Nal, G4 = Thr, G5 = Asp, G6 = D—Ala, G7 = Gly-β-Ala, G8 = Pro, G9 = Glu, F1 = Ser, F2 = His, F3 = h-Phe, F4 = Gly, F5 = Gly, F6 = Asp, E1 = Tyr, E2 = Glu, E3 = Glu, E4 = Ile, E5 = Pro, E6 = Aib, E7 = Aib, E8 = Tyr, E9 = Cha, E10 = D—Glu]. Rt = 21.8 min (Sequence Id no. 4).

hirunorm-III of structure

Ile—Arg—Phe—Thr—Asp—D—Ala—Gly-β-Ala—Pro—Glu—Ser—His-h-Phe—Gly—Gly—Asp—Tyr—Glu—Glu—Ile—Pro—Aib—Aib—PO$_4$H$_2$—Phe—Cha—D—Glu—OH [compounds of formula (I) wherein G1 = Ile, G2 = Arg, G3 = Phe, G4 = Thr, G5 = Asp, G6 = D—Ala, G7 = Gly-β-Ala, G8 = Pro, G9 = Glu, F1 = Ser, F2 = His, F3 = h-Phe, F4 = Gly, F5 = Gly, F6 = Asp, E1 = Tyr, E2 = Glu, E3 = Glu, E4 = Ile, E5 = Pro, E6 = Aib, E7 = Aib, E8 = PO$_4$H$_2$—Phe, E9 = Cha, E10 = D—Glu], using Boc—Phe(PO$_4$(CH$_3$)$_2$)—OH.Rt = 20.5 min; chromatographic purity >99% (Sequence Id no. 5).

EXAMPLE 3

The capability of the products described in the present invention of interfering in the coagulation cascade was evaluated using on human plasma:

a) APTT measurements (Babson, A. L. et al., Am. J. Clin. Path. 62, 856, (1974), Lenahan, J. G. et al., Clin. Chem., 12, 269, (1966) Miale, J. B, Laboratory Medicine: hematology, 6th edition, C. V. Mosby Co. (1982);

b) PT measurements (Quick, A. J. et al., Am. J. Med. Sci., 190, 501, (1935), Shapiro, S. et al., Coagulation, Thrombosis Brooklyn Medical Press, N.Y. (1949);

c) TT measurements (Exner, T. et al., Am. J. Clin. Pathol., 71, 521, 1979.

The inhibition of the hydrolysis, mediated by thrombin, of Chromozym TH by the peptides of the present invention was evaluated according to the literature (Stone, S. R., Hofsteenge, J., Biochemistry, 25, 4622, (1986).

In vitro determination of the peptide resistance to enzyme hydrolysis by thrombin.

97.2 nmol of hirunorm-I (286 μg), hirunorm-II (285 μg), hirunorm-III (293 μg), were incubated separately with 0.972 nmol of human a-thrombin (35 μg, 3110 Units NIH/mg) in 800 μL of 0.05M Tris/HCl buffer, 0.1M NaCl at pH-7.8 and a temperature of 37° C. 50 μL Aliquots were diluted with 200 μL of 100 mN H$_3$PO$_4$ and analyzed at pre-set times by capillary electrophoresis on a 0.75 μm×60 fused silica Waters capillary, using a Waters Quanta 4000 apparatus fitted with an UV detection at 214 nm. The analyses were carried out at a constant voltage of 18 KV, using a 100 mN phosphoric acid buffer for 25 min. The eluted peaks were collected and analyzed by Fab mass spectrometry.

In vitro determination of the peptides resistance to hydrolysis by plasma proteases.

1.94 nmol of hirunorm-I (571 μg), hirunorm-II (569 μg), hirunorm-III (585 μg), were separately incubated with 1600 μL of human plasma from heal thy donors at 37° C. for different times. 50 μL aliquots were added with 200 μL of 100 mN H$_3$PO$_4$. The supernatants were analyzed at pre-set times by HPLC on a Vydac C18 0.46×25 cm column with a straight acetonitrile gradient containing 0.1% (v/v) of trifluoroacetic acid (phase B) against 0.1% (v/v) aqueous trifluoroacetic acid (phase A), from 5 to 70% in B in 35 min at a flow rate of 1 mL/min, with detection at 210 nm. The eluted peaks were collected and analyzed by capillary electrophoresis on a 0.75 μm×60 cm fused silica Waters capillary, fitted with a UV detector at 214 nm. The analyses were carried out at a constant voltage of 18 KV, using a buffer 100 mN acid phosphoric for 25 min. The eluted peaks were then analyzed by means of Fab mass spectrometry.

The inhibition of platelet aggregation thrombin-mediated by the peptides of the present invention was evaluated according to Zucker M. B., Methods in Enzymology, vol. 169, 117–133 and Mustard, J. F. Kinlough-Rathbone, R. L., Packham, M. A., Methods in Enzymology, vol. 169, 3–11.

Comparison of the biological and kinetic parameters of the compounds of the invention with hirudin.

| Compound | PT+ | TT+ | APTT+ | IC$_{50}$* | $t_t^!$ | $t_p^!$ | $K_i^°$ |
|---|---|---|---|---|---|---|---|
| Hirunorm-I | 1.6 | 0.23 | 2.7 | 2.0 | >480 | 300 | 97. |
| Hirunorm-II | 0.32 | 0.022 | 0.27 | 1.0 | >480 | 480 | 2.6 |
| Hirunorm-III | 0.16 | 0.013 | 0.18 | 1.0 | >480 | 480 | 1.0 |
| Hirunorm-IV | — | — | — | — | >480 | — | 2.6 |
| Hirunorm-V | — | — | — | — | >480 | — | 1.0 |
| r-Hirudin$ | 1.8 | 0.086 | 0.90 | — | — | — | — |

+PT, APTT and TT are evaluated as the percent change compared with the control (no inhibitors) and in the table the inhibitor doses (μM) causing a 150%, 250% and 250% increase, respectively, are reported.
*IC$_{50}$ corresponds to the inhibitor doses (nM) causing a 50% decrease of the platelet aggregation.
!The factors $t_t$ and $t_p$ are the halving times (min) of the inhibitor concentrations in the presence of equimolar amounts of thrombin, respectively both alone and in human plasma.
°The hydrolysis inhibition constants of a chromogenic substrate are expressed as nM.
$Hirudin obtained by the recombinant technology.

We claim:
1. Peptides of general formula (I):
G1-G2-G3-G4-G5-G6-G7-G8-G9-F1-F2-F3-F4-F5-F6-E1-E2-E3-E4-E5-E6-E7-E8-E9-E10
wherein:

G1 - Ile, Val, Leu, Cha, Chg, alle, Nle, Pro, Pip, Phe, Tyr, Trp, Pgl, 1-Nal, 2-Nal, Met G2 - Arg, Val, L-Pap, L-Map, Ala, Ile, Leu, Lys, Orn, Thr, aThr, alle, Ser G3 - 2-Nal, Phe, 1-Nal, Trp, Tyr, Cha, Pgl, Chg G4 - Thr, Ser, Asn, Gln, His, aThr G5 - Asp, Glu G6 - D-Ala, Aib, Gly, Ac₆c, Ac₅c G7 - ε-Aca, δ-Ava, β-Ala-β-Ala, β-Ala-β-Ac₅c, β-Ala-β-Ac₆c, β-Ala—Gly, β-Ala-Gaba, Gly-β-Ala, Gly—Gly, Gly-Gaba, Gly-δ-Ava, Gaba-Gly, Gaba-β-Ala, δ-Ava-Gly, Gly—Gly—Gly G8 - Pro, Ala, Gly, Ac₆c, Ac₅c G9 - Glu F1 - Ser, Asn, Gln, Thr, aThr, His, h-Ser, h-Phe F2 - His F3 = h-Phe, Leu, Asp, Asn, Gly, Nle, Ile, alle, Val, Cha, Chg, Phe, Tyr, Pgl, Trp, 1-Nal, 2-Nal, Met, Deg, Dpg F4 = Gly, Asp, Asn F5 - Gly, Ala, D-Ala, Deg, Dpg F6 - Asp E1 - Tyr, Phe, Trp, Cha, His, Pgl, 1-Nal, 2-Nal, Chg E2 - Glu E3 - Glu, Pro, Sar, Hyp, Δ-Pro, thioprolone, Pip, Azt E4 - Ile, Chg, Cha, E5 - Pro, Sar, Hyp, Δ-Pro, thioproline, Pip, Azt E6 - Aib, Ala, Ac₆c, Ac₅c, Ac₄c,Ac₃c, cis or trans Δ-Glu, (S) or (R)-α-Me—Glu, Asp, Glu E7 - Aib, Ala, Ac₆c, Ac₅c, Ac₄c, Ac₃c, cis or trans Δ-Glu, (S) or (R)-α-Me—Glu, Asp, Glu E8 - Tyr, cis or trans Δ-Tyr, (S) or (R)-α-Me—Tyr, Phe, Aib, Ala, para or meta NO₂—Phe, para or meta SO₃H—Phe, para or meta PO₃H₂—Phe, para or meta PO₄H₂—Phe, para or meta SO₄H—Phe, meta SO₃H—Tyr, meta PO₃H₂—Tyr, para or meta CH₂PO₃H₂—Phe, para or meta CH₂SO₃H—Phe, para or meta CH₂COOH—Phe, para or meta CO₃H—Phe E9 - Cha, Leu, cis or trans Δ-Leu, (S) or (R) α-Me—Leu E10 = D-Glu, Glu, β-Ala, Asp, D-Asp, Gly, Ala, Gln, Gla, and salts thereof.

2. Peptides according to claim 1 wherein:

G1 = Ile or Val or Leu or Cha or Chg or alle or Nle or Pro or Phe or Tyr or Trp or Pgl or 1-Nal or 2-Nal or Met; G2 = Arg or L—Pap or L—Map or Val or Thr or Ile or Ala or Ser; G3 = 2-Nal or Phe or 1-Nal or Trp or Tyr; G4 = Thr; G5 = Asp; G6 = D—Ala; G7 = Gly-β-Ala or β-Ala-β-Ala; G8 = Pro; G9 = Glu, F1 = Ser or Asn or h-Ser or h-Phe; F2 = His; F3 = Nle or Cha or Met or h-Phe; F4 = Gly; F5 = Gly; F6 = Asp; E1 = Tyr or Phe; E2 = Glu; E3 = Glu or Pro; E4 = Ile; E5 = Pro; E6 = Aib; E7 = Aib; E8 = Tyr or PO₄H₂—Phe; E9 = Cha or Leu; E10 = D—Glu or Glu.

3. Peptides according to claim 1 wherein:

G1 = Chg or Ile or Val or alle or Nle or Phe or Tyr or Trp or Pgl or 1-Nal or 2-Nal; G2 = Arg or Val; G3 = 2-Nal or Phe or 1-Nal; G4 = Thr; G5 = Asp; G6 = D—Ala; G7 = Gly-β-Ala; G8 = Pro; G9 = Glu; F1 = Ser; F2 = His; F3 = Nle or h-Phe; F4 = Gly; F5 = Gly; F6 = Asp; E1 = Tyr or Phe; E2 = Glu; E3 = Glu or Pro; E4 = Ile; E5 = Pro; E6 = Aib; E7 = Aib; E8 = Tyr or PO₄H₂—Phe; E9 = Cha or Leu; E10 = D—Glu or Glu.

4. Peptide according to claim 1, having Sequence Id no. 1 wherein Ala in position 6 is D-Alar Ala in positions 7 and 8 is β-Ala; Xaa in positions 22 and 23 is Aib.

5. Peptide according to claim 1, having Sequence Id no. 2 wherein Ala in position 6 is D-Ala; Ala in position 8 is β-Ala; Phe in position 13 is h-Phe; Xaa in positions 22 and 23 is Aib; Xaa in position 25 is Cha; Glu in position 26 is D-Glu OH.

6. Peptide according to claim 1, having Sequence Id no. 3 wherein Xaa in position 1 is Chg; Xaa in position 3 is 2-Nal; Ala in position 6 id D-Ala; Ala in position 8 is β-Ala; Phe in position 13 is h-Phe; Xaa in positions 22 and 23 is Aib; Xaa in position 25 is Cha; Glu in position 26 is D-Glu OH.

7. Peptide according to claim 1, having Sequence Id no. 4 wherein Xaa in position 1 is Chg; Xaa in position 3 is 2-Nal; Ala in position 6 is D-Ala; Ala in position 8 is β-Ala; Phe in position 13 is h-Phe; Xaa in position 22 and 23 is Aib; Xaa in position 25 is Cha; Glu in position 26 is D-Glu OH.

8. Peptide according to claim 1, having Sequence Id no. 5 wherein Ala in Position 6 is D-Ala; Ala in position 8 is β-Ala; Phe in position 13 is h-Phe; Xaa in positions 22 and 23 is Aib; Phe in position 24 is PO₄H₂-Phe; Xaa in position 25 is Cha; Glu in position 26 is D-Glu OH.

9. A peptide according to claim 1, 2, 3, 4, 5, 6, 7 or 8 which is labeled with a radioisotope for ex vivo imaging of fibrin of platelet thrombi.

* * * * *